US010398480B2

(12) United States Patent
Stevenson et al.

(10) Patent No.: US 10,398,480 B2
(45) Date of Patent: Sep. 3, 2019

(54) INSTRUMENT AND METHOD FOR RESTORING MOTION TO A POLYAXIAL SCREW

(71) Applicant: Alphatec Spine, Inc., Carlsbad, CA (US)

(72) Inventors: Tara Stevenson, La Jolla, CA (US); Wally Gillespie, Carlsbad, CA (US); Clark Hutton, Carlsbad, CA (US)

(73) Assignee: Alphatec Spine, Inc., Carlsbad, CA (US)

( * ) Notice: Subject to any disclaimer, the term of this patent is extended or adjusted under 35 U.S.C. 154(b) by 363 days.

(21) Appl. No.: 15/205,062

(22) Filed: Jul. 8, 2016

(65) Prior Publication Data

US 2016/0317196 A1 Nov. 3, 2016

Related U.S. Application Data

(63) Continuation-in-part of application No. 14/056,573, filed on Oct. 17, 2013, now Pat. No. 9,408,643.

(60) Provisional application No. 61/716,413, filed on Oct. 19, 2012.

(51) Int. Cl.

*A61B 17/70* (2006.01)
*A61B 17/29* (2006.01)

(52) U.S. Cl.

CPC ...... *A61B 17/7082* (2013.01); *A61B 17/7035* (2013.01); *A61B 17/7091* (2013.01); *A61B 2017/2925* (2013.01)

(58) Field of Classification Search

CPC ........................ A61B 17/7082; A61B 17/7091
See application file for complete search history.

(56) References Cited

U.S. PATENT DOCUMENTS 7,481,813 B1 1/2009 Purcell
2009/0163962 A1 6/2009 Dauster et al.

*Primary Examiner* — Olivia C Chang
(74) *Attorney, Agent, or Firm* — Honigman LLP

(57) ABSTRACT

A polyaxial screw head remobilizer system for remobilizing a screw body member relative to a head of a polyaxial bone screw includes a barrel body, a handle assembly, an inner shaft, a slide assembly, and a lever. The barrel body includes proximal and distal ends. The distal end includes a plurality of prongs for releasably engaging a plurality of yokes of the polyaxial screw body member to center the inner shaft over the head of the screw. The handle assembly couples to the proximal end of the barrel body. The inner shaft, disposed within the barrel body, includes proximal and distal ends. An engagement feature of the inner shaft mates with pockets of a bushing of the screw body member. The slide assembly is operably coupled to the barrel body and effect translations of the inner shaft. The lever extends from the slide assembly and rotates to actuate the slide assembly.

14 Claims, 8 Drawing Sheets

100 500 101 106 105 108 133 102 112 110 124 111

110 124 229 228 125 222 234 230

110
111
102
125
124
108
127
105
107
112
122
106
133
133
101

INSTRUMENT AND METHOD FOR RESTORING MOTION TO A POLYAXIAL SCREW

CROSS-REFERENCE TO RELATED APPLICATIONS

This application is a continuation-in-part of U.S. patent application Ser. No. 14/056,573 filed on Oct. 17, 2013, which claims priority from U.S. Provisional Application Ser. No. 61/716,413 filed on Oct. 19, 2012 and entitled "Instrument and Method for Restoring Motion to a Polyaxial Screw" which is incorporated by reference in its entirety herein.

FIELD

The present invention relates generally to an apparatus for internal fixation of the spine and, more specifically, to a remobilizer for restoring polyaxial motion to a polyaxial screw head that has been locked.

BACKGROUND

Certain spinal conditions, including a fracture of a vertebra and a herniated disc, indicate treatment by spinal immobilization. Several methods of spinal immobilization are known, including surgical fusion and the attachment of pins and bone plates to the affected vertebras.

Spinal immobilization systems typically require the threaded securement of some form of bone anchor or bone screw-assembly into two or more vertebrae, which entails the drawing of the rod to the anchors/screw-assemblies, or drawing the anchors/screw-assemblies to the rod. Spinal screw-assemblies are used to secure a stabilization rod and comprise various components including a pedicle screw and a body member. The design of the spinal screw-assemblies allows for variable angular movement of the body member with respect to the pedicle screw with a threaded shaft portion of the screw extending through an opening in an end of the body member.

The next generation of pedicle screws is polyaxial screws, with a body member which pivots and rotates about the spherical head of a bone screw. The bone screw is captured in the body member with a bushing; the bushing in turn accepts a rod after the screw has been placed in the pedicle, and the rod is captured in the bushing/body member assembly by inserting a set screw into the threads of the body member. As with most polyaxial pedicle screws, tightening of the set screw applies pressure onto the rod, which translates pressure onto the bushing, which then applies pressure on the spherical head of the bone screw, locking the polyaxial motion. Unlike other polyaxial pedicle screws, the new pedicle screw achieves additional locking because of the design of the screw bushing; the lower portion of the bushing acts like a wedge so when force is applied, the bottom of the bushing wedges between the spherical head of the bone screw and the body member, providing additional locking force.

While this feature provides optimum performance with regards to strength of the construct in maintaining correction, it can make screw removal difficult, since the polyaxial motion remains locked due to the wedging effect, even after the set screw is removed. In order to restore polyaxial motion, the bushing must be un-wedged from between the bone screw head and the body member. The wedge can be knocked loose by tapping the body member of the bone screw with enough force to break the friction lock of the wedge, but this method may not be considered feasible in the case of patients with very poor bone.

As a result, a tool is needed which can interact with the bushing and pull up on it, restoring the bushing to its position prior to locking and thereby removing the wedge and restoring polyaxial motion.

Previously there has been no reliable method for restoring polyaxial motion to the screw. There has been no feature on the pedicle screw or bushing which allowed a tool to apply an upward force and remove the wedge. Tools have been attempted which rotate the bushing to "break" the wedge force, but these caused damage to the bushings and could not reliably effect the unlocking. The method of tapping on the screw body member to "break" the wedge has already been identified as one which cannot be recommended for patients with poor bone quality.

SUMMARY OF THE INVENTION

Provided herein are apparatuses, systems, and methods of use for a polyaxial screw head remobilizer.

The polyaxial screw head remobilizer system for remobilizing a screw body member relative to a head of a polyaxial bone screw generally comprises a polyaxial screw assembly, a barrel body, a handle assembly, an inner shaft, a slide assembly, and a lever.

The barrel body has a proximal end and a distal end. In some embodiments, the distal end of the barrel body includes engagement features configured to engage with a plurality of yokes of a polyaxial screw body member and a polyaxial screw, so as to center the polyaxial screw head remobilizer on the head of the screw. The engagement features may comprise rounded rectangular prongs positioned on the distal end, such that the prongs may be seated in yokes of the screw body member. The barrel body may be made from any suitable material as known in the art including, by way of example and not limitation, stainless steel, a thermoplastic or other materials. The barrel body is generally cylindrical in shape; however, it may assume alternative shapes such as square, rectangular, polygonal, and the like.

The handle assembly is coupled to the proximal end of the barrel body for holding of the polyaxial screw head remobilizer by an operator. The handle assembly may be coupled to the barrel body by any suitable method of attachment such as, for example, a fastener, an aperture, a nut or bolt connection, or the like. In some embodiments, the handle assembly further comprises a mount arm, fixedly coupled to the handle assembly and the barrel body, the mount arm configured to retain the slide assembly. In some embodiments, the mount arm has an aperture adapted to receive the inner shaft. In some embodiments, the mount arm is configured to slidably couple with the slide assembly, such as, without limitation, by a rail or track. In some embodiments, the mount arm further comprises a pin or other structure configured to limit the degree of distal translation of the inner shaft.

The inner shaft is disposed within the barrel body. The distal end of the inner shaft further comprises an engagement feature. The engagement feature is configured to permit positioning of the barrel body and inner shaft within the polyaxial screw body member, engagement of the engagement feature with a polyaxial screw bushing, application of a force to unlock the screw bushing, disengagement of the inner shaft from the polyaxial screw bushing, and removal of the remobilizer from the polyaxial screw body member. In one embodiment, the engagement feature is a plurality of extensions configured to couple with a plurality of pockets of the polyaxial screw bushing. In some embodiments, the inner shaft further comprises a helical trough disposed near the proximal end of the inner shaft.

The inner shaft is generally rounded-rectangular in cross-section. However, the inner shaft may assume alternative shapes, such as circular, square, cylindrical, polygonal, and the like, having an engagement feature that is adapted for entry into the screw body member and to frictionally lock with the pockets of the bushing. Alternatively, the inner shaft may be any shape which may be customized for the particular barrel body utilized. The inner shaft may be made from any suitable material as known in the art including, by way of example and not limitation, stainless steel, a thermoplastic or other materials. In many embodiments, the inner shaft is fixedly coupled to a stop element.

The slide assembly is slidably coupled to the handle assembly (and/or the mating arm) and the inner shaft. In some embodiments, the mount arm and slide assembly may have apertures configured to permit a portion of the inner shaft to be disposed therethrough. In many embodiments, the proximal end of the inner shaft is fixedly coupled to a stop element, the stop element positioned proximal the slide assembly. The stop element is configured to impede translation of the slide assembly proximally along the inner shaft. In some embodiments, the slide assembly further comprises a pin configured to interact with the helical trough of the inner shaft. In use, the interaction of the pin with the helical trough causes rotation of the inner shaft as the pin travels the length of the trough.

The lever rotatably associates with the slide assembly. The lever may extend from the slide assembly via mechanical attachment by any suitable method of attachment, for example, a fastener, an aperture, a nut-bolt connection, a washer, or the like. The lever is further pivotally coupled to the handle assembly by a suitable mechanical attachment, such as a pin or the like. The inner shaft may be slidably disposed within the barrel body and configured such that the inner shaft may be longitudinally displaced within the barrel body by actuation of the lever and the slide assembly.

In a further embodiment, a spring member is operably coupled to the lever and the handle assembly, such that the spring member urges the lever from an actuated position back to its original position subsequent to actuation of the lever in either the proximal or distal direction.

In use, when the lever is actuated, the lever causes the slide assembly to slide proximally along the inner shaft. As the slide assembly translates, the rotation pin coupled to the slide assembly engages with the helical trough on the inner shaft, causing the inner shaft to rotate as the pin travels the length of the trough. The rotation of the inner shaft causes the engagement feature to couple with pockets of the screw bushing. Once the pin has traveled the full length of the helical trough, the slide assembly reaches the stop element, configured to impede translation of the slide assembly along the inner shaft. Once the slide assembly reaches the stop, continued proximal translation of the slide assembly also translates the stop proximally. Because the stop is fixedly coupled to the proximal end of the inner shaft, the inner shaft is also translated proximally. Because the engagement feature of the inner shaft is coupled with the pockets of the screw bushing, the bushing is pulled proximally, thereby releasing its fixation on the head of the screw. Thus, the polyaxial screw assembly is remobilized.

A polyaxial pedicle screw assembly comprises a screw body member, a screw bushing, and a polyaxial pedicle screw. The screw body member is generally cylindrical in configuration and adapted to receive a head portion of the pedicle screw. The bushing is adapted to fit within the screw body member between the screw body member and the head portion, and prevent polyaxial motion of the screw when the bushing is locked or pressed into position. The bushing further comprises pockets configured to engage with the inner shaft of the remobilizer.

The bushing of the polyaxial screw was designed with undercut pockets to give the remobilizer tool a means of attachment. The remobilizer has an outer tube which can be inserted into the yokes of the screw body member to center the tool on the head of the screw. Inside the outer tube is a shaft which has extensions on the tip which, when rotated, can be inserted in the pockets of the bushing. The tip is actuated by squeezing the handle; squeezing the handle first pulls a pin in the inner shaft up a helical trough, causing the tip to rotate 90 degrees and inserting the extensions into the mating bushing pockets. Once the pin has traveled the full distance of the helical trough, it hits a stop, such that continuing to squeeze the handle then pulls the tip of the shaft towards the handles. Since the shaft is now mated with the bushing, this pulls the bushing upwards as well, removing the wedge from the bone screw and body member and restoring polyaxial motion. Releasing the handle restores the tip to its original position so it can be removed from the screw.

A method of using the polyaxial screw head remobilizer tool comprises the steps of: inserting an outer tube of the remobilizer into yokes of a screw body member to center the tool and an inner shaft disposed within the outer tube on a head of the screw, in proximity to a bushing member of the screw body; actuating the tool to rotate the inner shaft such that an engagement feature on the tip of the inner shaft mates with a plurality of pockets in the bushing member of the screw; continuing actuation of the tool such that a force is applied to the bushing member to release a fixation hold between the bushing, the screw head, and the screw body member, thereby remobilizing the screw head; releasing the actuation of the tool such that the inner shaft derotates and the engagement feature at the tip of the inner shaft disengages from the pockets in the bushing member of the screw; and removing the remobilizer tool from the screw body member.

The apparatuses, systems, and methods of use are set forth in part in the description which follows, and part will be obvious from the description or can be learned by practice of the methods, apparatuses, and systems. The advantages of the methods, apparatuses, and systems will be realized and attained by means of the elements and combinations particularly pointed out in the appended claims. It is to be understood that both the foregoing general description and the following detailed description are exemplary and explanatory only and are not restrictive of the methods, apparatuses, and systems, as claimed.

BRIEF DESCRIPTION OF THE DRAWINGS

In the accompanying figures, like elements are identified by like reference numerals among the several preferred embodiments of the present invention.

DETAILED DESCRIPTION OF THE INVENTION

The foregoing and other features and advantages of the invention are apparent from the following detailed description of exemplary embodiments, read in conjunction with the accompanying drawings. The detailed description and drawings are merely illustrative of the invention rather than limiting, the scope of the invention being defined by the appended claims and equivalents thereof.

The words proximal and distal are applied to denote specific ends of components of the current invention described herein. A proximal end refers to the end of a component nearer to a medical professional when operating the component. A distal end refers to the end of the component further from the medical professional when operating the component.

Figure 1:
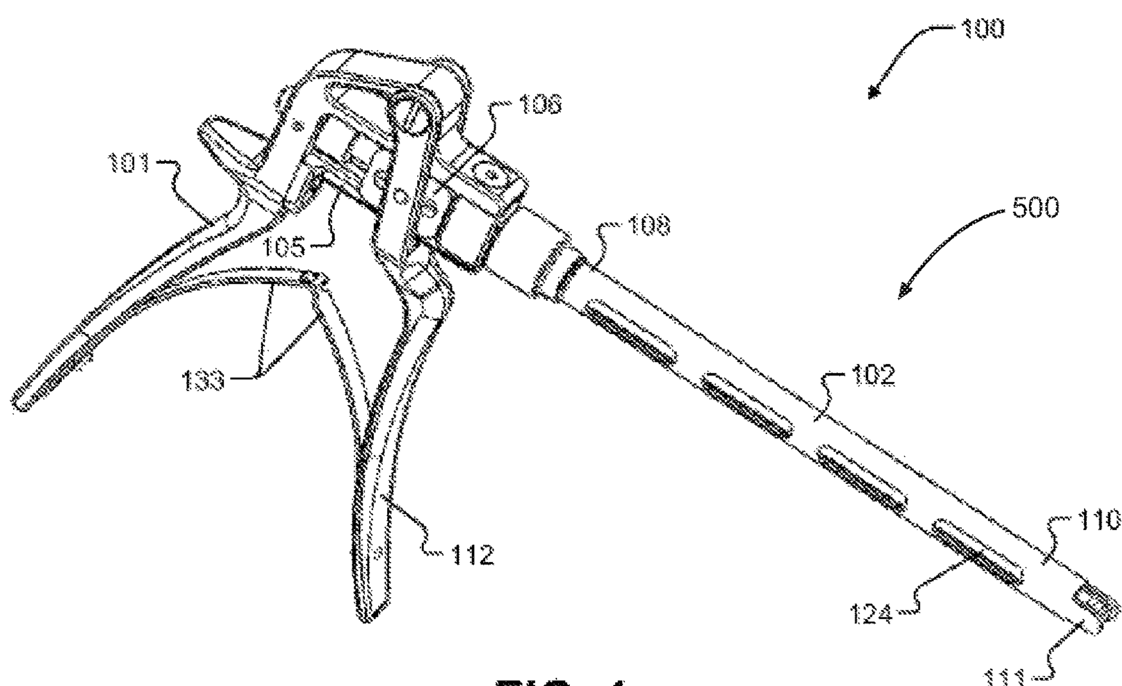
FIG. 1 is an illustration of one embodiment of the polyaxial screw head remobilizer.
Figure 2:
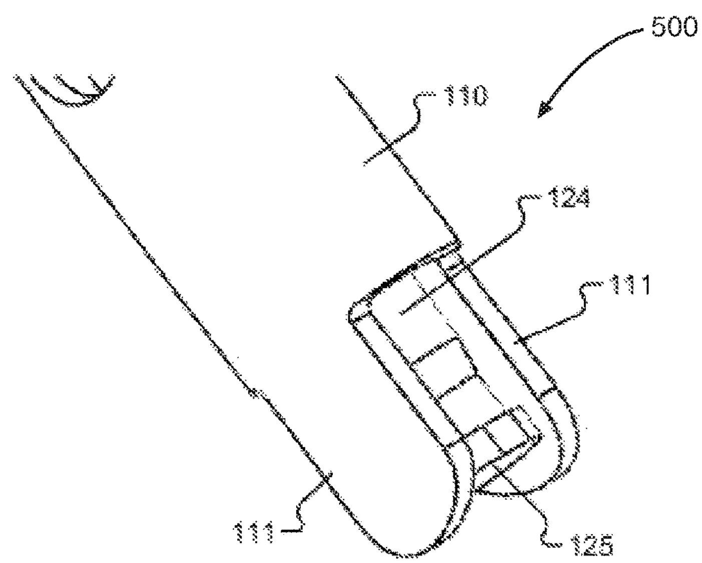
FIG. 2 is a close up view of the distal end of the remobilizer of FIG. 1.
Figure 6:
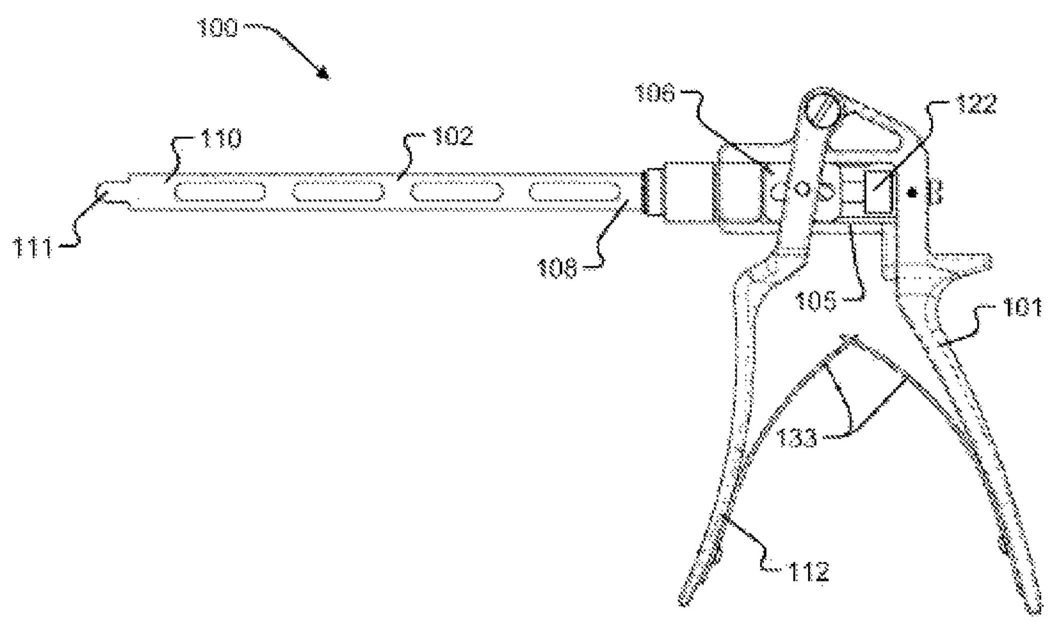
FIG. 6 is a side view of one embodiment of the polyaxial screw head remobilizer.
Figure 11:
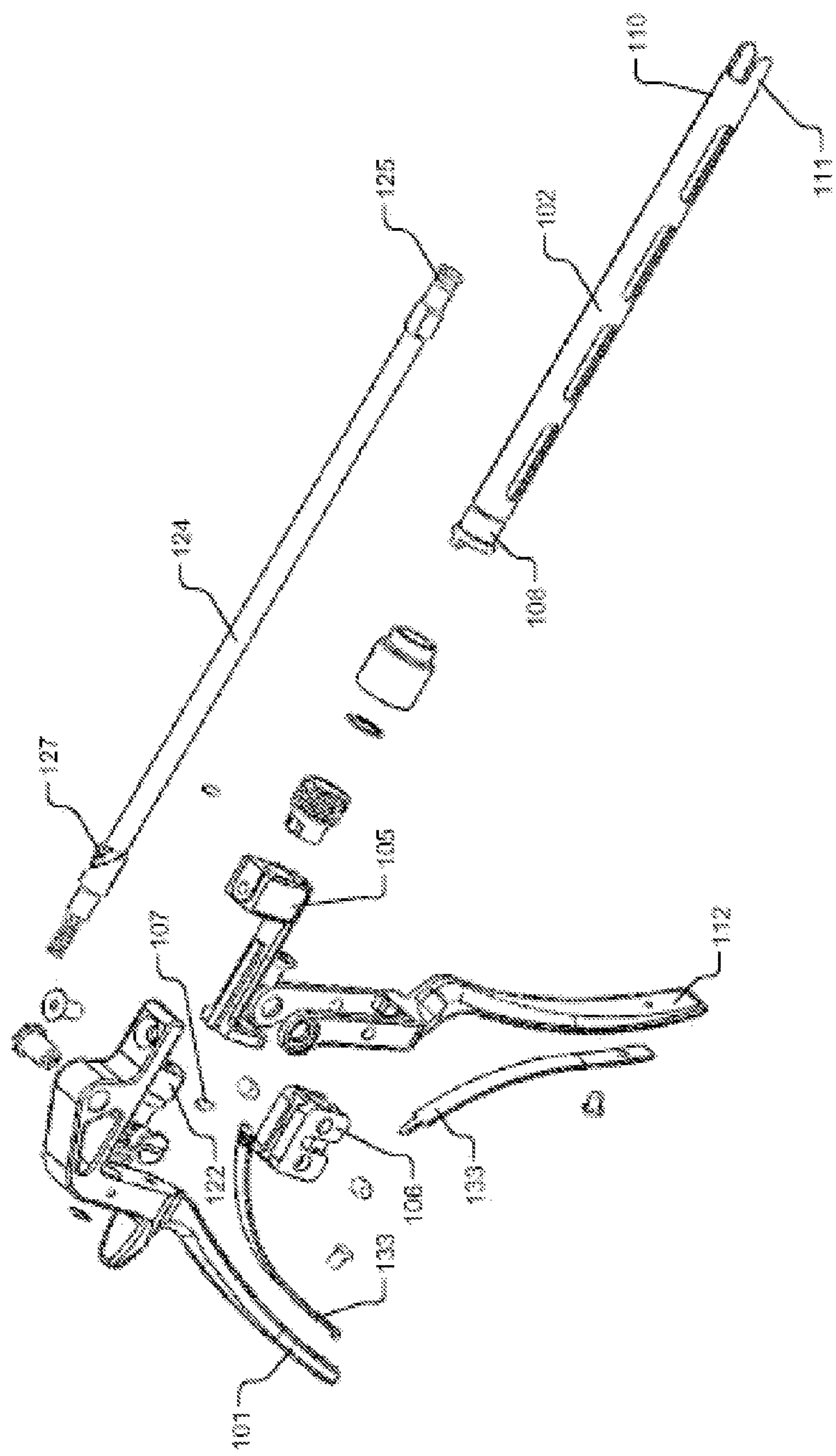
FIG. 11 is an exploded view of one embodiment of the polyaxial screw head remobilizer.

As shown in FIGS. 1, 6, and 11, a polyaxial screw head remobilizer system 500 includes a polyaxial screw head remobilizer 100 generally comprises a barrel body 102, a handle assembly 101 operably coupled to a slide assembly 106, an inner shaft 124 coaxially disposed within the barrel body, and a lever 112 operably coupled to the slide assembly. Generally speaking, the screw head remobilizer 100 interacts with a bushing of a polyaxial screw assembly and longitudinally displaces the bushing to restore the bushing to an unlocked position, thereby removing the bushing wedge, and restoring polyaxial motion of a screw.

The barrel body 102 has a generally longitudinal axis, wherein the barrel body 102 includes a proximal end 108 and a distal end 110 generally along the longitudinal axis. As shown in FIGS. 1-2 and 5-11, the distal end 110 of the barrel body 102 includes engagement features 111 configured to engage with a plurality of yokes (or U-shaped channels) 223 of a polyaxial screw body member 222 and a polyaxial screw 230, so as to center the polyaxial screw head remobilizer 100 on the head of the screw 230. The engagement features 111 may comprise rounded rectangular prongs positioned on the distal end 110, such that the prongs 111 may be seated in the yokes 223 of the screw body member 222. In alternative embodiments, the engagement features 111 may comprise any shape suitable for seating in the yokes 223 of the screw body member 222, such as, without limitation, rectangular, square, triangular, ovoid, polygonal, and/or the like. Preferably, the engagement features 111 are shaped such that, when engaged, the yokes 223 are not permitted to rotate about an axis. The barrel body 102 may be made from any suitable material as known in the art including, by way of example and not limitation, stainless steel, a thermoplastic or other materials. The barrel body 102 is generally cylindrical in shape; however, it may assume alternative shapes such as square, rectangular, polygonal, and the like.

The handle assembly 101 is coupled to the proximal end 108 of the barrel body 102 for holding of the polyaxial screw head remobilizer 100 by an operator. The handle assembly 101 may be coupled to the barrel body 102 by any suitable method of attachment such as, for example, a fastener, a rivet, an aperture, a nut or bolt connection, or the like. In some embodiments, the handle assembly 101 further comprises a mount arm 105, fixedly coupled to the handle assembly 101 and the barrel body 102, the mount arm 105 configured to retain the slide assembly 106. In some embodiments, the mount arm 105 has an aperture adapted to receive the inner shaft 124. In some embodiments, the mount arm 105 is configured to slidably couple with the slide assembly 106, such as, without limitation, by a rail or track. In some embodiments, the mount arm 105 further comprises a pin or other structure configured to limit the degree of distal translation of the inner shaft 124.

Figure 9:
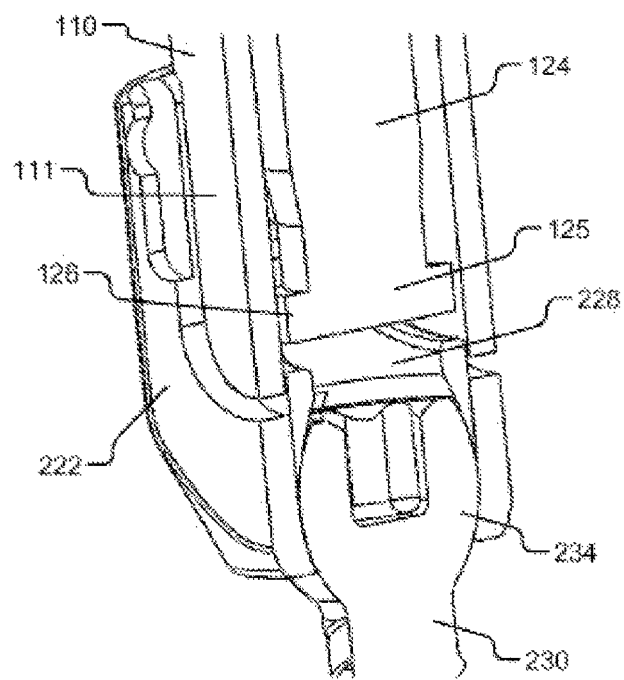
FIG. 9 is a cutaway view of a remobilizer tip inserted in a polyaxial screw, upon initial insertion.
Figure 10:
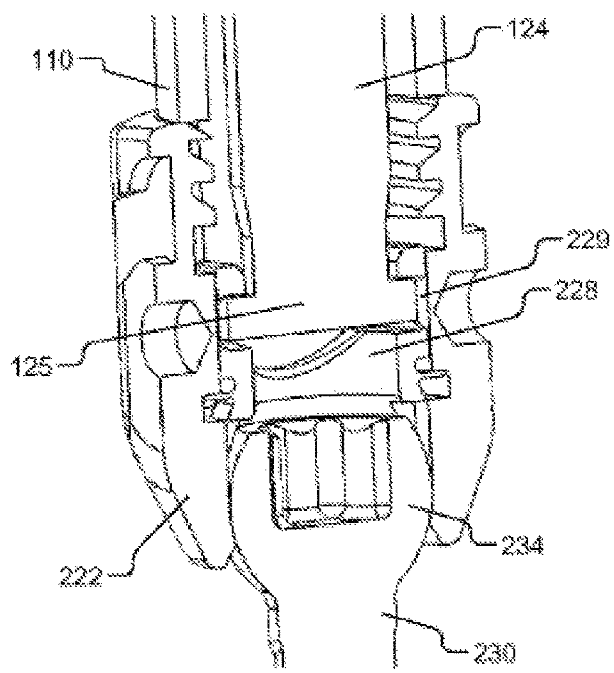
FIG. 10 is a cutaway view of a remobilizer tip inserted in a polyaxial screw after rotation of the remobilizer tip into bushing pockets of the screw.

The inner shaft 124 is coaxially disposed within the barrel body 102 and longitudinally displaced therein. The distal end of the inner shaft 124 further comprises an engagement feature 125. As shown in FIGS. 9 and 10, the engagement feature 125 is configured to permit positioning of the barrel body 102 and inner shaft 124 within the polyaxial screw body member 222, engagement of the engagement feature 125 with a polyaxial screw bushing 228, application of a force to unlock the screw bushing 228, disengagement of the inner shaft 124 from the polyaxial screw bushing 228, and removal of the remobilizer 100 from the polyaxial screw body member 222.

Figure 3A:
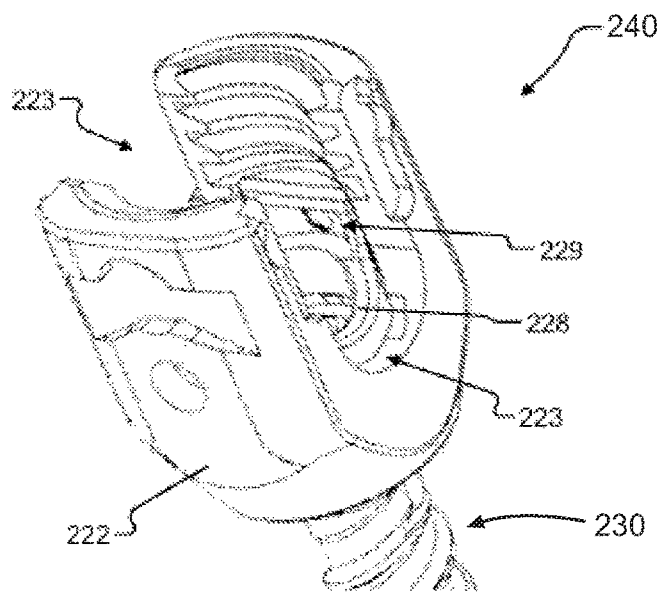
FIG. 3A is an isometric view of a polyaxial screw for use with the remobilizer.
Figure 3B:
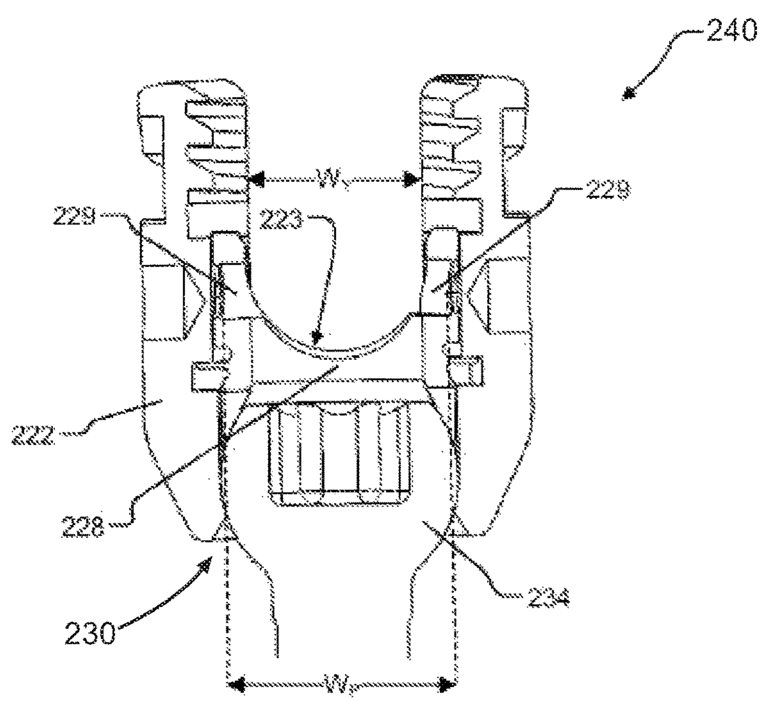
FIG. 3B is a cutaway view of a polyaxial screw for use with the remobilizer.
Figure 4A:
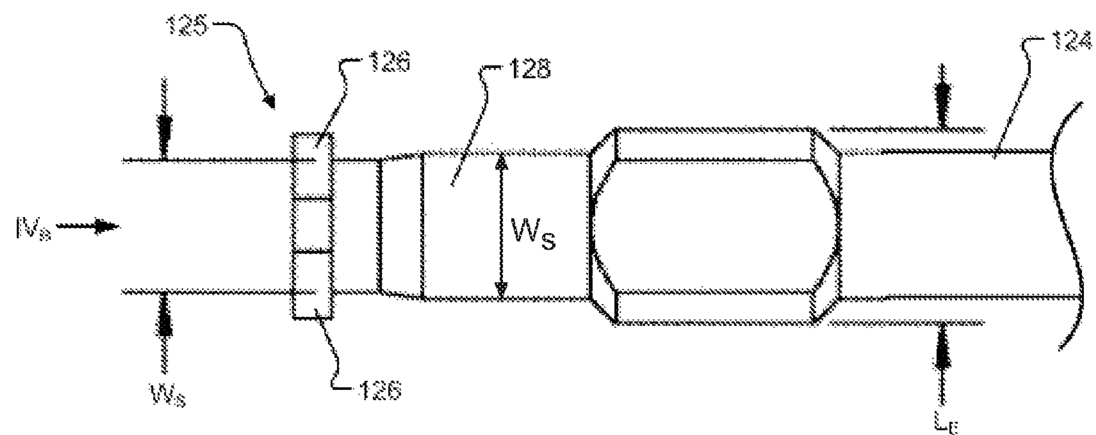
FIG. 4A is a side view of the distal end of the inner shaft.
Figure 4B:
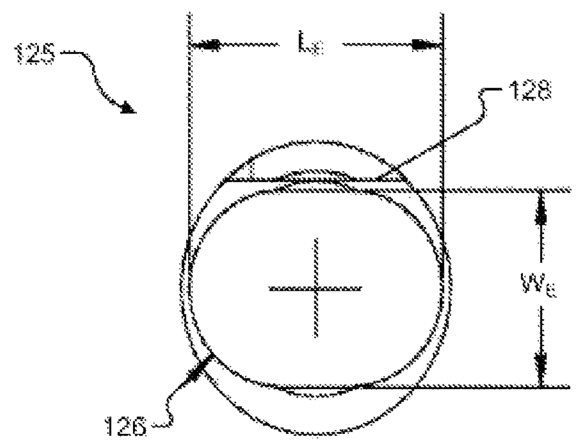
FIG. 4B is a side view of the distal end of the inner shaft taken from view IVB in FIG. 4A.
Figure 5:
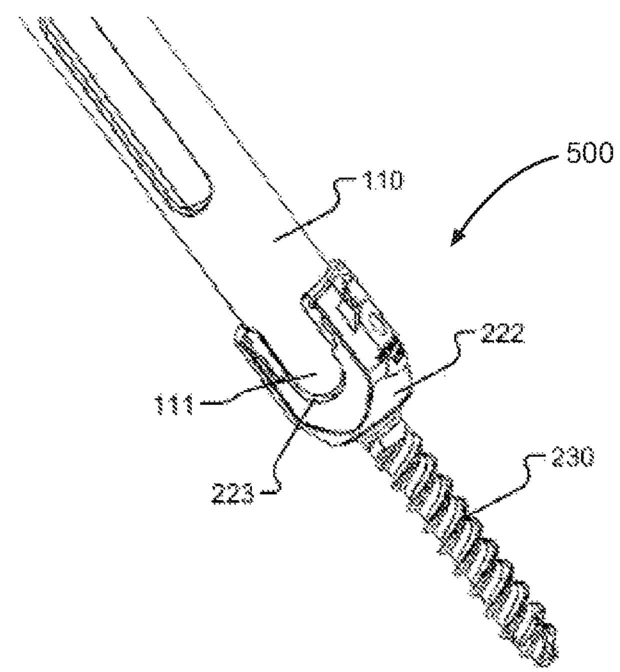
FIG. 5 is a close up view of the distal end of the tube of the remobilizer, coupled to a polyaxial screw.

In one embodiment, as shown in FIGS. 4A and 4B, the engagement feature 125 includes a plurality of extensions 126 configured with a stepped down portion 128 on the distal end of the inner shaft 124. The stepped down portion 128 allows the engagement feature 125 to coaxially pass through the plurality of yokes 223, whereby the stepped down portion 128 includes a Width $W_S$ that is less than a Length $L_E$ of the engagement feature 125 and the inner shaft. The engagement feature 125 includes a width $W_E$, whereby the length $L_E$ is greater than the Width $W_E$, as shown in FIGS. 4A and 4B. Preferably, the Width $W_E$ is less than the Width $W_Y$ of the yokes 223, such that the engagement feature 125 may longitudinally pass through the Width $W_Y$ of the yokes 223, as shown in FIG. 3B. Preferably, the Length $L_E$ is greater than the Width $W_Y$ of the yokes 223, such as to engage with a plurality of pockets 229 of the polyaxial screw bushing 228 (as shown in FIGS. 3A-3B and 9-10) when the inner shaft 124 is rotated after the extensions 126 pass through the yokes 223.

Preferably, a quarter-turn rotation of the inner shaft 124 engages the extensions 126 with the plurality of pockets 229. In one embodiment, the plurality of pockets 229 include a Width $W_P$ that is greater than the Width $W_Y$ of the yokes 223, and preferably, the Width $W_P$ is about the length $L_E$ of the engagement feature 125, as shown in FIG. 3B, such as to allow fixedly engagement of the engagement feature 125 and the plurality of pockets 229. As such, the engagement feature 125 is able to unlock the bushing 228 that wedges the screw head 234 by locking with the plurality of pockets 229 and longitudinally moving the bushing proximally away from the screw head 234 and restoring polyaxial motion of the screw 230. In alternative embodiments, the engagement feature 125 may comprise generally rectangular lips. More generally, the engagement feature 125 may have any shape suitable for mating with the particular shape of the pockets 229 of the bushing 228. For example, and without limitation, the engagement feature 125 could be rounded, domed, square, triangular, and/or the like.

Figure 7:
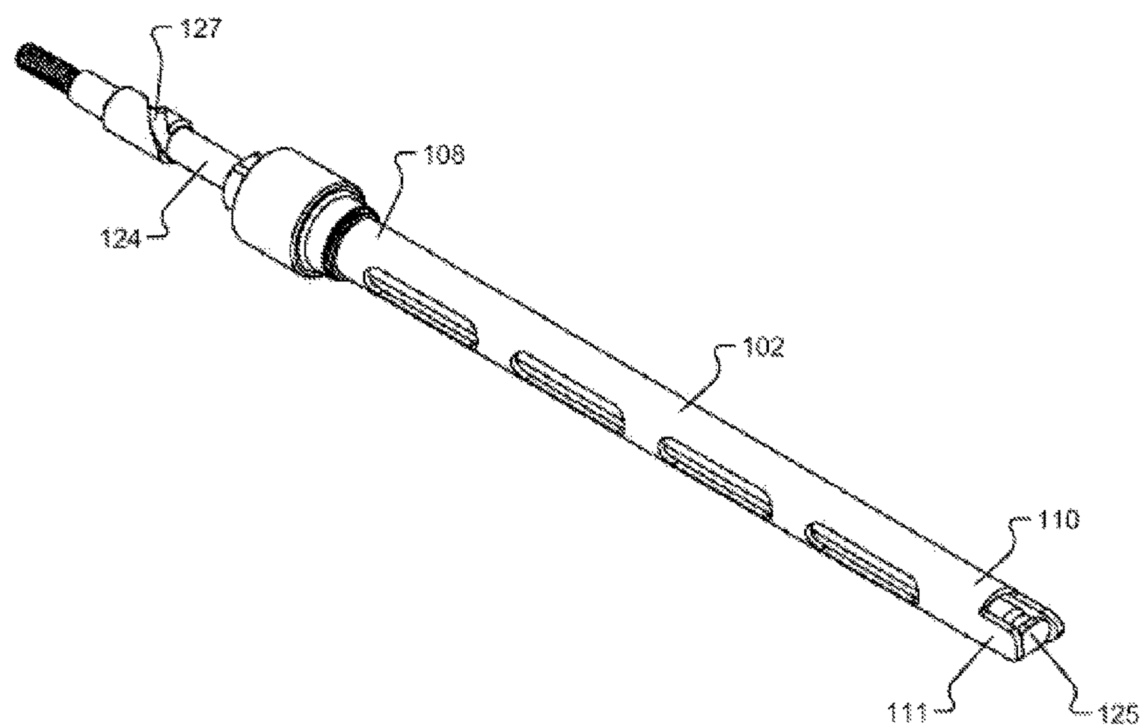
FIG. 7 is a perspective view of one embodiment of the barrel body and the inner shaft, the inner shaft having an engagement feature at a distal end and a helical trough near a proximate end.
Figure 8:
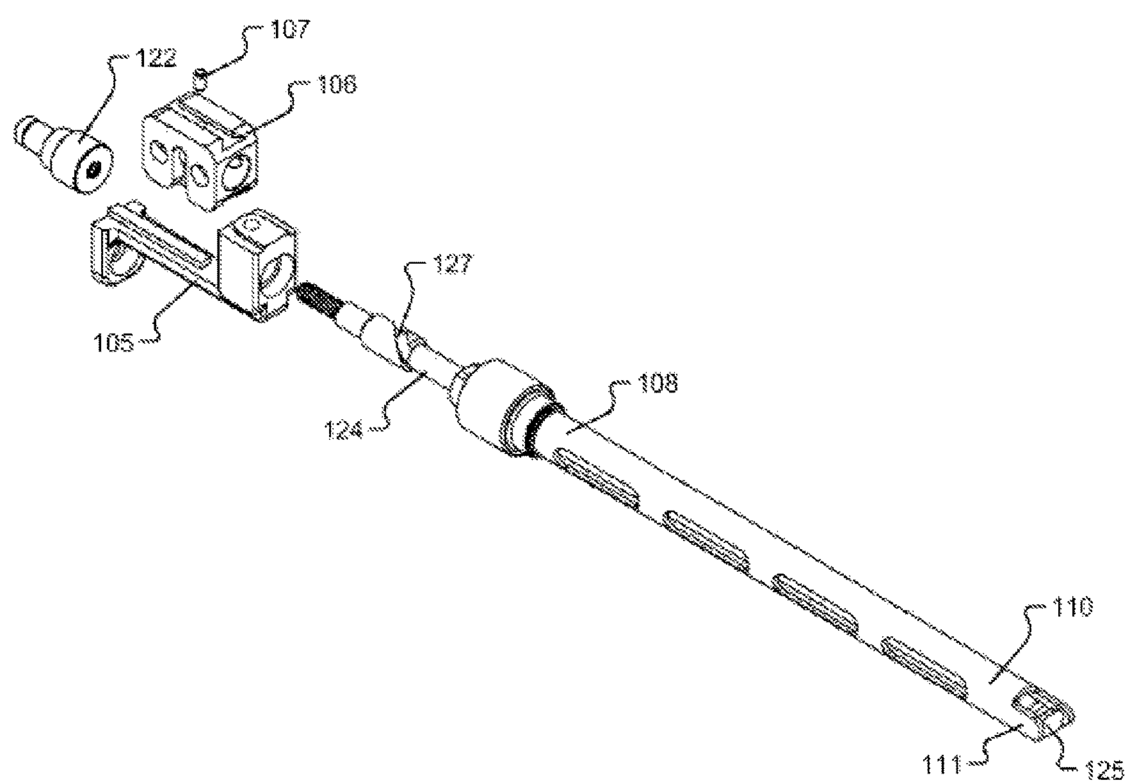
FIG. 8 is an exploded view of the barrel body, inner shaft, mount arm, slide assembly, and stop element.

As shown in FIGS. 7 and 8, in many embodiments, the inner shaft 124 further comprises a helical trough 127 disposed near the proximal end of the inner shaft 124. FIG. 7 shows the inner shaft 124 disposed within the barrel body 102, with the helical trough 127 disposed proximally from the proximate end 108 of the barrel body 102. The inner shaft 124 is generally rounded-rectangular in cross-section. However, the inner shaft 124 may assume alternative shapes, such as circular, square, cylindrical, polygonal, and the like, having an engagement feature 125 that is adapted for entry into the screw body member 222 and to frictionally lock with the pockets 229 of the bushing 228. Alternatively, the inner shaft 124 may be any shape which may be customized for the particular barrel body 102 utilized. The inner shaft 124 may be made from any suitable material as known in the art including, by way of example and not limitation, stainless steel, a thermoplastic or other materials. In some embodiments, the proximal end of the inner shaft 124 may be fixedly coupled to a stop element 122. The inner shaft 124 may be fixedly coupled to the stop element 122 by any suitable method of attachment such as, for example, a threaded element, a fastener, a rivet, an aperture, a nut or bolt connection, or the like.

FIG. 8 shows an exploded view of the barrel body 102, inner shaft 124, slide assembly 106, stop element 122, and mating arm 105. The slide assembly 106 is slidably coupled to the handle assembly 101 (and/or the mating arm 105) and the inner shaft 124. In some embodiments, the mount arm 105 and slide assembly 106 may have apertures configured to permit a portion of the inner shaft 124 to be disposed therethrough. In many embodiments, the proximal end of the inner shaft 124 is fixedly coupled to the stop element 122, the stop element 122 positioned proximal the slide assembly 106. The stop element 122 is configured to impede translation of the slide assembly 106 proximally along the inner shaft 124. In some embodiments, the slide assembly 106 further comprises a pin 107 configured to interact with the helical trough 127 of the inner shaft 124, as the slide assembly 106 translates along the length of the inner shaft 124. In use, the interaction of the pin 107 with the helical trough 127 causes rotation of the inner shaft 124 as the pin 107 travels the length of the trough 127. In some embodiments, the helical trough 127 is configured to cause a 90 degree rotation of the inner shaft 124 as the remobilizer 100 is actuated. In some embodiments, the degree of rotation is any rotation sufficient to permit the engagement feature 125 to couple with the pockets 229 of the bushing 228.

The lever 112 rotatably associates with the slide assembly 106. The lever 112 may extend from the slide assembly 106 via mechanical attachment by any suitable method, including, for example, a fastener, an aperture, a nut-bolt connection, a washer, or the like. The lever 112 is further pivotally coupled to the handle assembly 101 by a suitable mechanical attachment, such as a pin or the like. The inner shaft 124 may be slidably disposed within the barrel body 102 and configured such that the inner shaft 124 may be longitudinally displaced within the barrel body 102 by actuation of the lever 112 and the slide assembly 106.

The lever 112 may assume any polygonal shape having a distal end that can be longitudinally displaced. The slide assembly 106 and the lever 112 may be made from any suitable material as known in the art including, by way of example and not limitation, stainless steel, a thermoplastic or other materials. In some embodiments, the lever 112 and the slide assembly 106 may be associated with a locking and/or moving mechanism 133 at the proximal end 108, for incrementally locking and/or proximally moving the inner shaft 124 towards the proximal end 108 and subsequently releasing the inner shaft 124 to be moved towards the distal end 110 of the barrel body 102. Alternative spring locked or spring hinged mechanisms may be coupled to the slide assembly 106 and the lever 112 to move the inner shaft 124 proximally and distally within the barrel body 102.

In one embodiment, the locking moving mechanism is a spring member 133*a*. The spring member 133*a* is operably coupled to the lever 112 and the handle assembly 101, such that the spring member 133*a* urges the lever 112 from an actuated position back to its original position subsequent to actuation of the lever 112 in either the proximal or distal direction.

In use, when the lever 112 is actuated, the lever 112 causes the slide assembly 106 to slide proximally along the inner shaft 124 and the mounting arm 105. As the slide assembly 106 translates, the pin 107 coupled to the slide assembly 106 engages with the helical trough 127 on the inner shaft 124, causing the inner shaft 124 to rotate as the pin 107 travels the length of the trough 127. The rotation of the inner shaft 124 causes the engagement feature 125 to couple with pockets 229 of the screw bushing 228. Once the pin 107 has traveled the full length of the helical trough 127, the slide assembly 106 reaches the stop element 122, configured to impede translation of the slide assembly 106 along the inner shaft 124. Once the slide assembly 106 reaches the stop 122, continued proximal translation of the slide assembly 106 also translates the stop 122 proximally. Because the stop 122 is fixedly coupled to the proximal end of the inner shaft 124, the inner shaft 124 is also translated proximally. Because the engagement feature 125 of the inner shaft is coupled with the pockets 229 of the screw bushing 228, the bushing 228 is pulled proximally, thereby releasing its fixation on the head of the screw 230. Thus, the polyaxial screw assembly is remobilized.

As shown in FIGS. 3A and 3B, a polyaxial pedicle screw assembly 240 comprises a screw body member 222, a screw bushing 228, and a polyaxial pedicle screw 230. Polyaxial pedicle screws are more fully disclosed in U.S. publication 2010/0318136, "Polyaxial bone screw assembly," and in U.S. publication 2008/0243189, "Variable Angle Spinal Screw Assembly" both of which are hereby incorporated by reference in their entirety. The screw body member 222 is generally cylindrical in configuration and adapted to receive a head portion 234 of the pedicle screw 230. The screw body member 222 further comprises a plurality of yokes 223, adapted to receive engagement features 111 of the distal end 110 of the barrel body 102. Generally, the screw body member 222 has a generally tulip shape to form U-shaped yokes 223; however, the screw body member 222 may have alternative shapes to form the yokes 223. In alternative embodiments, the screw body member 222 may have other shapes, such as rectangular, square, diamond, and/or the like. The bushing 228 is adapted to fit within the screw body member 222 between the screw body member 222 and the head portion 234, and prevent polyaxial motion of the screw 230 when the bushing 228 is locked or pressed into position. The bushing 228 further comprises pockets 229 configured to mate with an engagement feature 125 at the distal end of the inner shaft 124 of the remobilizer 100. The pockets 229 generally have a rectangular lipped shape; however, in alternative embodiments, the pockets 229 may have any shape suitable for mating with the engagement feature 125 of the inner shaft 124, such as square, round, domed, circular, rectangular, triangular, slot, and/or the like.

FIG. 9 shows the prongs 111 of the barrel body 102 and the engagement feature 125 of the inner shaft 124 coupled with the screw body member 222, prior to the lever 112 being actuated. The engagement feature 125 is aligned with the prongs 111, so that the barrel body 102 and inner shaft 124 may be inserted into the screw body member 222.

FIG. 10 shows the engagement of the engagement feature 125 with the bushing pockets 229 as the lever 112 is actuated and the slide assembly 106 initially reaches the stop element 122. The inner shaft 124 has been rotated 90 degrees to couple the engagement feature 125 with the bushing pockets 229. In some embodiments, the degree of rotation is any rotation sufficient to permit the engagement feature 125 to couple with the pockets 229 of the bushing 228. At this stage, if actuation of the lever 112 is continued, the engagement feature 125 will exert an upward force on the bushing 228, thereby releasing the bushing 228 from fixation with the screw head 234, remobilizing the polyaxial screw assembly 240.

In some embodiments, the degree of rotation is any rotation sufficient to permit the engagement feature 125 to couple with the pockets 229 of the bushing 228.

FIG. 11 shows an exploded view of the polyaxial screw head remobilizer 100 with like reference numerals mentioned previously.

A method of using the polyaxial screw head remobilizer tool comprises the steps of: inserting an outer tube of the remobilizer into yokes of a screw tulip to center the tool and an inner shaft disposed within the outer tube on a head of the screw, in proximity to a bushing member of the screw body; actuating the tool to rotate the inner shaft such that an engagement feature on the tip of the inner shaft mates with a plurality of pockets in the bushing member of the screw; continuing actuation of the tool such that a force is applied to the bushing member to release a fixation hold between the bushing, the screw head, and the screw tulip, thereby remobilizing the screw head; releasing the actuation of the tool such that the inner shaft derotates and the engagement feature at the tip of the inner shaft disengages from the pockets in the bushing member of the screw; and removing the remobilizer tool from the screw tulip.

While the invention has been described in connection with various embodiments, it will be understood that the invention is capable of further modifications. This application is intended to cover any variations, uses or adaptations of the invention following, in general, the principles of the invention, and including such departures from the present disclosure as within the known and customary practice within the art to which the invention pertains.

We claim:

1. A polyaxial screw head remobilizer system, comprising:

- a polyaxial screw assembly including a polyaxial screw body member that includes a yoke, a polyaxial screw member, and a polyaxial bushing member; and
- a remobilizer tool, the remobilizer tool comprising:
  - a barrel body having a proximal end and a distal end;
  - a handle assembly coupled to the proximal end of the barrel body;
  - an inner shaft having a proximal end and a distal end, the inner shaft disposed within the barrel body, wherein the distal end of the inner shaft further comprises an engagement feature configured to mate with at least one pocket of the bushing member of the polyaxial screw assembly, wherein the engagement feature includes a Length LE and a Width WE, whereby the Length LE is greater than the Width WE and the Width WE is less than a Width WY of the yoke, such that the engagement feature may longitudinally pass through the Width WY of the yoke;
  - a slide assembly operably coupled to the barrel body, the slide assembly configured to effect translation of the inner shaft; and
  - a lever extending from the slide assembly, the lever being rotatable to actuate the slide assembly;
  - wherein actuation of the slide assembly rotates the engagement feature of the inner shaft to engage the at least one pocket of the polyaxial bushing member;
  - wherein the engagement features of the inner shaft are a plurality of prongs;
  - wherein one of the plurality of prongs is configured to releasably engage the yoke;
  - wherein the engagement feature further comprises a plurality of extensions configured with a stepped down portion on the distal end of the inner shaft; and
  - wherein the stepped down portion allows the engagement feature to coaxially pass through the yoke.

2. The system of claim 1, wherein the Length LE is greater than the Width WY of the yoke, such that the Length LE of the engagement feature engages with the at least one pocket of the polyaxial bushing member of the polyaxial screw assembly.

3. The system of claim 2, wherein the at least one pocket includes a Width WP that is greater than the Width WY of the yoke, and the Width WP is about the length LE of the engagement feature, to allow the engagement feature to unlock the bushing from a head of the polyaxial screw member.

4. The system of claim 3, wherein the handle assembly further comprises a mount arm fixedly coupled to the handle assembly, the mount arm configured to retain the slide assembly and the mount arm further comprises an aperture adapted to receive the inner shaft.

5. The system of claim 4, wherein the mount arm is configured to slidably couple with the slide assembly.

6. The system of claim 5, wherein the mount arm further comprises a pin or other structure configured to limit the degree of distal translation of the inner shaft.

7. The system of claim 1, further comprising a spring member operably coupled to the lever and the handle assembly, such that the spring member urges the lever from an actuated position back to its original position subsequent to actuation of the lever in either the proximal or distal direction.

8. The system of claim 1, wherein the polyaxial bushing member is disposed between the polyaxial screw body member and a head of the polyaxial screw member.

9. The system of claim 8, wherein actuation of the slide assembly rotates the engagement feature of the inner shaft to engage the at least one pocket of the polyaxial bushing member and longitudinally displaces the inner shaft towards the proximal end to proximally translate the polyaxial bushing member disposed between the polyaxial screw body member and the head of the polyaxial screw member, remobilizing the head of the polyaxial screw member.

10. The system of claim 1, wherein the inner shaft further comprises a helical trough configured to interact with a pin coupled to the slide assembly so as to rotate the inner shaft as the slide assembly translates along the inner shaft.

11. The system of claim 10, further comprising a stop member fixedly coupled to the proximal end of the inner shaft, wherein the stop member is configured to impede proximal translation of the slide assembly along the inner shaft such that continued proximal translation of the slide assembly also translates the inner shaft proximally.

12. The system of claim 11, wherein the lever further comprises a polygonal shape having a distal end that can be longitudinally displaced.

13. The system of claim 1, further comprising a locking or moving mechanism associated with the lever and the slide assembly and located at the proximal end of the barrel body, for incrementally locking or proximally moving the inner shaft towards the proximal end of the barrel body and subsequently releasing the inner shaft to be moved towards the distal end of the barrel body.

14. The system of claim 1, further comprising a spring locked or spring hinged mechanism coupled to the slide assembly and the lever, to move the inner shaft proximally and distally within the barrel body.

* * * * *